(12) United States Patent
Haecker et al.

(10) Patent No.: US 10,702,646 B2
(45) Date of Patent: Jul. 7, 2020

(54) MEDICAL FLUID CASSETTE AND MEDICAL HOSE SET WITH A MEDICAL FLUID CASSETTE

(71) Applicant: FRESENIUS MEDICAL CARE DEUTSCHLAND GMBH, Bad Homburg (DE)

(72) Inventors: Juergen Haecker, Neu-Anspach (DE); Stephan Goessmann, Frankfurt (DE)

(73) Assignee: PRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 144 days.

(21) Appl. No.: 15/120,922

(22) PCT Filed: Feb. 24, 2015

(86) PCT No.: PCT/EP2015/053783
§ 371 (c)(1),
(2) Date: Aug. 23, 2016

(87) PCT Pub. No.: WO2015/128306
PCT Pub. Date: Sep. 3, 2015

(65) Prior Publication Data
US 2016/0361486 A1    Dec. 15, 2016

(30) Foreign Application Priority Data
Feb. 26, 2014   (DE) .................. 10 2014 002 578

(51) Int. Cl.
*B01D 46/00*    (2006.01)
*A61M 1/36*     (2006.01)
*A61M 1/14*     (2006.01)

(52) U.S. Cl.
CPC ............ *A61M 1/3621* (2013.01); *A61M 1/14* (2013.01); *A61M 1/3627* (2013.01);
(Continued)

(58) Field of Classification Search
CPC ............ A61M 1/34–3496; A61M 1/14; A61M 1/3621; A61M 1/3627; A61M 1/3639;
(Continued)

(56) References Cited

U.S. PATENT DOCUMENTS 3,935,111 A * 1/1976 Bentley ................. A61M 5/165
                                              210/446
4,444,661 A * 4/1984 Jackson ................. B01D 29/05
                                              210/446
(Continued)

FOREIGN PATENT DOCUMENTS

DE    102009018664    2/2012
WO    WO 2008/065472   6/2008
(Continued)

*Primary Examiner* — T. Bennett McKenzie
(74) *Attorney, Agent, or Firm* — Jacobson Holman, PLLC

(57) ABSTRACT

The invention relates to a medical fluid cassette and a medical hose set having a medical fluid cassette for receiving and/or carrying a medical fluid. The invention relates in particular to a blood hose set having a medical fluid cassette for the extracorporeal blood treatment. An easily manufactured insert having a clot filter is proposed, this insert being inserted or pushed into a receptacle, for example, a groove, in the interior of a chamber of the housing body of the medical fluid cassette.

11 Claims, 3 Drawing Sheets

(52) U.S. Cl.
CPC ....... *A61M 1/3639* (2013.01); *A61M 2205/12* (2013.01); *A61M 2205/121* (2013.01); *A61M 2205/123* (2013.01); *A61M 2205/125* (2013.01); *A61M 2205/3331* (2013.01); *A61M 2205/75* (2013.01)

(58) Field of Classification Search
CPC ........ A61M 2205/12; A61M 2205/121; A61M 2205/123; A61M 2205/125; A61M 2205/3331; B01D 46/00; B01D 46/0002–0017
USPC .......................................................... 96/155
See application file for complete search history.

(56) References Cited

U.S. PATENT DOCUMENTS

| | | | | |
|---|---|---|---|---|
| 5,160,332 | A | * | 11/1992 | Nomura .............. A61M 1/3627 210/436 |
| 5,401,262 | A | * | 3/1995 | Karwoski ........... A61M 1/0001 604/321 |
| 5,472,605 | A | * | 12/1995 | Zuk, Jr. ............... A61M 1/3627 210/433.1 |
| 2004/0127841 | A1 | | 7/2004 | Briggs |
| 2010/0100034 | A1 | * | 4/2010 | Wich-Heiter ........... A61M 1/14 604/29 |
| 2010/0269702 | A1 | | 10/2010 | Brueckner et al. |
| 2010/0270230 | A1 | | 10/2010 | Brueckner et al. |

FOREIGN PATENT DOCUMENTS

| WO | WO 2010/121819 | 10/2010 |
|---|---|---|
| WO | WO 2012/017417 | 2/2012 |

* cited by examiner

MEDICAL FLUID CASSETTE AND MEDICAL HOSE SET WITH A MEDICAL FLUID CASSETTE

TECHNICAL FIELD

The invention relates to a medical fluid cassette and a medical hose set with a medical fluid cassette for receiving and/or carrying a medical fluid. In particular the invention relates to a blood hose set with a medical fluid cassette for the extracorporeal blood treatment.

BACKGROUND

Medical fluid cassettes for receiving and/or carrying a medical fluid are known from the prior art. The document WO 2010/121819 A1 discloses a blood cassette to be used for an extracorporeal blood treatment; it has at least one housing body and at least one chamber integrated into the housing body for receiving and/or carrying medical fluids and at least one channel integrated into the housing body for receiving and/or carrying a medical fluid. A clot filter is integrated into the known blood cassette in another separate chamber downstream from an air bubble separation chamber, which is integrated into the housing body. However, the space required for this known integration of the clot filter into the housing body limits the remaining available space for other structures to be integrated into the housing body, such as chambers for receiving and/or carrying medical fluids with the prevailing compact dimensions of the blood cassette, for example. In manufacturing the blood cassette, the known clot catcher is permanently connected to the housing body by flanging or by laser welding.

In addition, fluid cassettes designed as bubble chambers having a cylindrical or conical clot filter upstream from the outlet opening of the air bubble separation chamber are known from the prior art. For example, one such air bubble separation chamber is known from the document WO 2008/065472 A1. One disadvantage of this known air bubble separation chamber with an integrated clot catcher can be seen in the complicated production due to the complex geometry. Another disadvantage may be seen in the low dwell volume and the small flow cross section downstream from the clot filter openings.

DESCRIPTION OF THE INVENTION

One object of the present invention is to provide a medical fluid cassette for receiving and/or carrying a medical fluid, which will overcome at least one of the aforementioned disadvantages or one of the aforementioned limitations.

Another object of the present invention is to provide a blood cassette having an integrated clot catcher which overcomes at least one of the aforementioned disadvantages or one of the aforementioned limitations.

Another object of the present invention is to integrate components having a complex geometry into a medical fluid cassette without flanging or welding and thus to reduce the complexity of manufacturing.

The objects are achieved with the features of the instant invention and the advantageous embodiments characterized below.

The present invention provides a medical fluid cassette having a housing body, which forms a first wall section of a chamber for receiving and/or carrying a medical fluid, a cover which forms a second wall section of the chamber, an insert with a first peripheral section and a second peripheral section, wherein the insert is designed for at least partially filling up a cross section of the chamber, wherein the cross section of the chamber is bordered at least by the first wall section and the second wall section, and wherein the insert subdivides the chambers into a first chamber section and a second chamber section and a receptacle in and/or on the first wall section, wherein the receptacle is designed for accommodating the first peripheral section, and said first peripheral section is accommodated in the receptacle.

The first wall section borders an interior of the chamber in at least some sections. The first wall section borders the chamber in the region of the receptacle in particular. The housing body may have a mounting face, and the chamber may be designed as a cavity in the mounting face, so that the chamber forms a recess in the mounting face. The mounting face may form a bordering edge of the chamber in at least some sections and/or may protrude beyond the edge of the border in at least some sections. The second wall section borders an interior of the chamber in at least some sections. In particular the second wall section borders the chamber in the region of the receptacle. For example, the surface of the cover facing the chamber borders the interior of the chamber in at least some sections. The cover may cover the recess formed by the chamber in the mounting face and may cover the bordering edge of the recess and may also cover a region outside of the bordering edge in at least some sections. The cover may thus cover the mounting face at least partially or even completely.

If the cover is designed as a flexible film, then the surface of the film facing the chamber borders an interior of the chamber in at least some sections. The film is particularly advantageously connected permanently to the mounting face in at least some sections. The film may be connected permanently to the mounting face in the region of the bordering edge, for example, and/or in the region outside of the bordering edge.

A permanent connection of the cover to the mounting face is understood in the present invention to refer to a connection which does not require any additional aids to be maintained after being joined.

The mounting face may be formed in a planar design in at least some sections or completely.

In special embodiments, the housing body may advantageously be manufactured from plastic, in particular polypropylene (PP), by injection molding or thermo-forming. The cover may be designed as a flexible film made of plastic, in particular polypropylene (PP). In such embodiments, the cover may be permanently connected to the mounting face by welding or adhesive bonding in at least some sections.

In some embodiments, the cover may sit loosely on the second peripheral section when the insert has been inserted into the receptacle and the cover is permanently connected to the mounting face. In such embodiments, there is no permanent connection between the second peripheral section and the second wall section. However, the second wall section may temporarily form a fluid-tight connection with the second peripheral section when the second wall section is pressed against the second peripheral section. This pressing may be accomplished, for example, during use of the medical fluid cassette as intended to receive and/or carry the medical fluid. When the pressing force is stopped, the connection is no longer fluid-tight. The pressing force may be applied in particular when the cover of the medical fluid cassette is coupled to a coupling face of a treatment device or a treatment machine.

In other embodiments, the second wall section may permanently form a fluid-tight connection with the second peripheral section. In such embodiments, the second wall section may be welded or adhesively bonded to the second peripheral section, so that no additional auxiliary aids are needed to maintain the fluid-tight connection. In such embodiments, the cover of the medical fluid cassette may also be coupled to a coupling face of a treatment device or a treatment machine. However, in this embodiment, no special pressing force is required to connect the second wall section to the second peripheral section.

The receptacle may be embodied in at least some sections as a groove and/or as a channel and/or as a stay and/or as a shoulder in or on the first wall section. The receptacle serves, on the one hand, to receive and/or to guide and/or to hold the first peripheral section in the intended position in the chamber of the medical fluid cassette during assembly of the medical fluid cassette. For example, the housing body with the insert may be assembled, for example, by inserting the insert into its final position in the receptacle before attaching the cover to the housing body because in this manufacturing state the housing body is half open and therefore is accessible from the outside.

The receptacle may be designed as a peripheral groove or as a peripheral channel or as a peripheral stay and/or as a peripheral shoulder in or on the first wall section. In such embodiments, the first peripheral section may be in fluid-tight connection with the receptacle when the insert is inserted into the receptacle.

In some embodiments, all the sections of the receptacle lie in a plane, so that a planar insert can be inserted. The thickness of the insert in the range of the first peripheral section is essentially constant.

In some embodiments, the receptacle is formed by two bordering surfaces, which lie in two parallel planes, wherein the space between the parallel planes is designed for insertion and/or for receiving the insert, and wherein the parallel planes intersect the first wall section and the second wall section. The shape of the insert is designed for insertion and/or for receiving the insert between the two bordering surfaces, at least in the area of the first peripheral section.

In special embodiments, the receptacle is formed by two bordering surfaces, which lie in two parallel planes, wherein the space between the parallel planes is designed for insertion and/or for receiving the insert, and wherein the parallel planes intersect the first wall section and/or the second wall section essentially at a right angle. Again in this embodiment, the shape of the insert is designed for insertion and/or for receiving the insert between the two bordering surfaces, at least in the area of the first peripheral section.

The second peripheral section may be designed to be straight, wherein the first peripheral section is then designed to curved or angular in at least some sections.

The insert may have at least one opening structure for fluid-permeable connection of the first chamber section to the second chamber section.

In special embodiments, the opening structure may have a clot filter.

In some embodiments, the first chamber section and/or the second chamber section may be designed as an air bubble separator.

One advantage of the present invention is that sliding in and/or insertion of the insert into the receptacle may be performed automatically by an industrial assembly robot in the manufacture of the medical fluid cassette. Alternatively, a manual sliding in and/or insertion of the insert into the receptacle is of course also facilitated because the receptacle and the insert are designed in accordance with fabrication and assembly procedures.

In certain embodiments, the medical fluid cassette may have a compact design and nevertheless at the same time be designed for measuring the pressure in the medical fluid both upstream from the clot filter and downstream from the clot filter, such that the pressure of the medical fluid on the flexible film can also be measured by connecting a pressure sensor to the cover from the outside. The measurement site upstream from the clot filter may also be arranged upstream from an air bubble filter, which is itself upstream from the clot filter. A pressure measurement is then possible upstream from the air bubble separator and downstream from the clot filter. This advantage is achieved by the fact that the clot filter is designed as an insert into the chamber in a space-saving design. Space is therefore available for the pressure measurement site on the flexible film in the medical fluid cassette upstream from the clot filter and downstream from the clot filter, and the medical fluid cassette is compact at the same time.

BRIEF DESCRIPTION OF THE FIGURES

One exemplary embodiment according to the present teaching is described below in greater detail with reference to the figures. Additional details and advantages are described further on the basis of the exemplary embodiment depicted in the figures. The reference numerals in the figures all have the same meanings.

FIG. 1 shows a clear-cut view (left figure) and a sectional diagram (right figure) of a detail of a medical fluid cassette (1) according to the invention with a housing body (100) and a chamber (200) integrated into the housing body. The chamber (200) has a first wall section (110). The first wall section (110) is part of the housing body (100) and borders the chamber (200) in the area of the receptacle (500) in particular. The housing body (100) has a mounting face to which the cover (300), which is a flexible film, is secured by welding in some sections, and the chamber (200) is designed as a cavity in the mounting face, so that the chamber (200) in the mounting face forms a recess. The mounting face forms a bordering edge (800) of the chamber (200) in a plane, wherein the bordering edge (800) borders the recess in at least some sections and wherein the mounting face protrudes beyond the bordering edge (800) in at least some sections. The second wall section (220) is part of the cover (300), and the surface of the cover (300) facing the chamber (200) borders the interior of the chamber (200) in at least some sections, in particular in the area of the receptacle (500). The cover (300) completely covers the recess formed by the chamber (200) in the mounting face and covers at least the bordering edge of the recess. In addition, the cover (300) covers regions of the mounting face outside of the bordering edge. In addition, the housing body (100) has a first fluid channel (600) and a second fluid channel (700), both of which are in flow connection with the chamber (200). In the present exemplary embodiment, the housing body is essentially a rigid injection-molded part made of plastic. The chamber (200), the first fluid channel (600) and the second fluid channel (700) are each open on a half-side with respect to an environment of the medical fluid cassette and are sealed by the cover (300), which is a flexible film in the present exemplary embodiment, with respect to the environment of the medical fluid cassette, during the fabrication of the medical fluid cassette. In the present exemplary embodiment, the flexible film is welded to the housing body (100) by means of laser welding, for example, at least along the bordering edge (800). FIG. 1 shows the cover (300), which is indicated only by the reference numeral and is cut open along the line which is drawn freely by hand, so that the chamber (200), the first fluid channel (600) and the second fluid channel (700) are visible. The first wall section (110) of the chamber (200) has a receptacle (500), namely a groove in the present exemplary embodiment, which is designed for insertion of an insert (400) before the welding of the cover (300) to the housing body (100). The insert (400) itself is not shown in FIG. 1. The insert (400) shown in FIG. 3 is in turn designed to be inserted into the receptacle (500) as long as there is still no cover (300) on the housing body (100). For this purpose, the insert (400) has a first bordering section (410), which is adapted to the contour of the first wall section (110) and the receptacle (500). In addition, the insert (400) has a second peripheral section (420), which is designed for fluid-tight contact with the cover (300) when the housing body is covered by the cover, and the cover (300) is pressed against the second peripheral section (420). The cover (300) is pressed only during the treatment of a medical fluid in a treatment machine, i.e., when the medical fluid cassette is in use. Before the use of the medical fluid cassette, the cover (300) sits loosely on the peripheral section (420). However, in other embodiments, it is also possible to connect the cover (300) to the peripheral section (420) in a fluid-tight connection during the fabrication of the medical fluid cassette (I) by welding or adhesive bonding, for example.

FIG. 2 shows a clear-cut perspective view of the medical fluid cassette according to FIG. 1, but with the insert (400) inserted, wherein, as already shown in FIG. 1, the cover (300) is again indicated in FIG. 2 only by the reference numeral and is cut open along the line that is drawn by free hand, so that the chamber (200), the first fluid channel (600), the second fluid channel (700) and the peripheral section (420) are visible. The peripheral section (410) is inserted in a fluid-tight manner into the receptacle (500), which is designed as a peripheral groove. The insert (400) has a clot filter (450), which connects the first chamber section (250) to the second chamber section (260) in a fluid-permeable connection. The clot catcher (450) is shown as round in the embodiment illustrated here.

In other particularly preferred embodiments, the clot catcher (450) may essentially or completely fill up the entire area of the insert (400). The cross-sectional area of the clot catcher (450) and/or of the insert (400) through which the blood flows can therefore be maximized and the venting when filling with medical fluid as well as the dissolution of air bubbles can be facilitated by the clot catcher (450) and/or the insert (400).

The chamber (200) in the present exemplary embodiment is designed as an air bubble separator for a blood cassette for the extracorporeal blood treatment. Advantages of the air bubble separator include the large chamber volume due to the space-saving arrangement of the clot catcher (450) and the large flow cross section with a particularly calm flow guidance, in particular in the first chamber section (250), which forms the lower area of the air bubble separator. Due to the calm flow guidance, smaller air bubbles adhering to the clot catcher (450) may combine to form larger air bubbles, which can become detached due to their greater buoyancy forces. Therefore, this facilitates the release of air bubbles from the clot catcher (450) and/or the insert (400).

Figure 1:
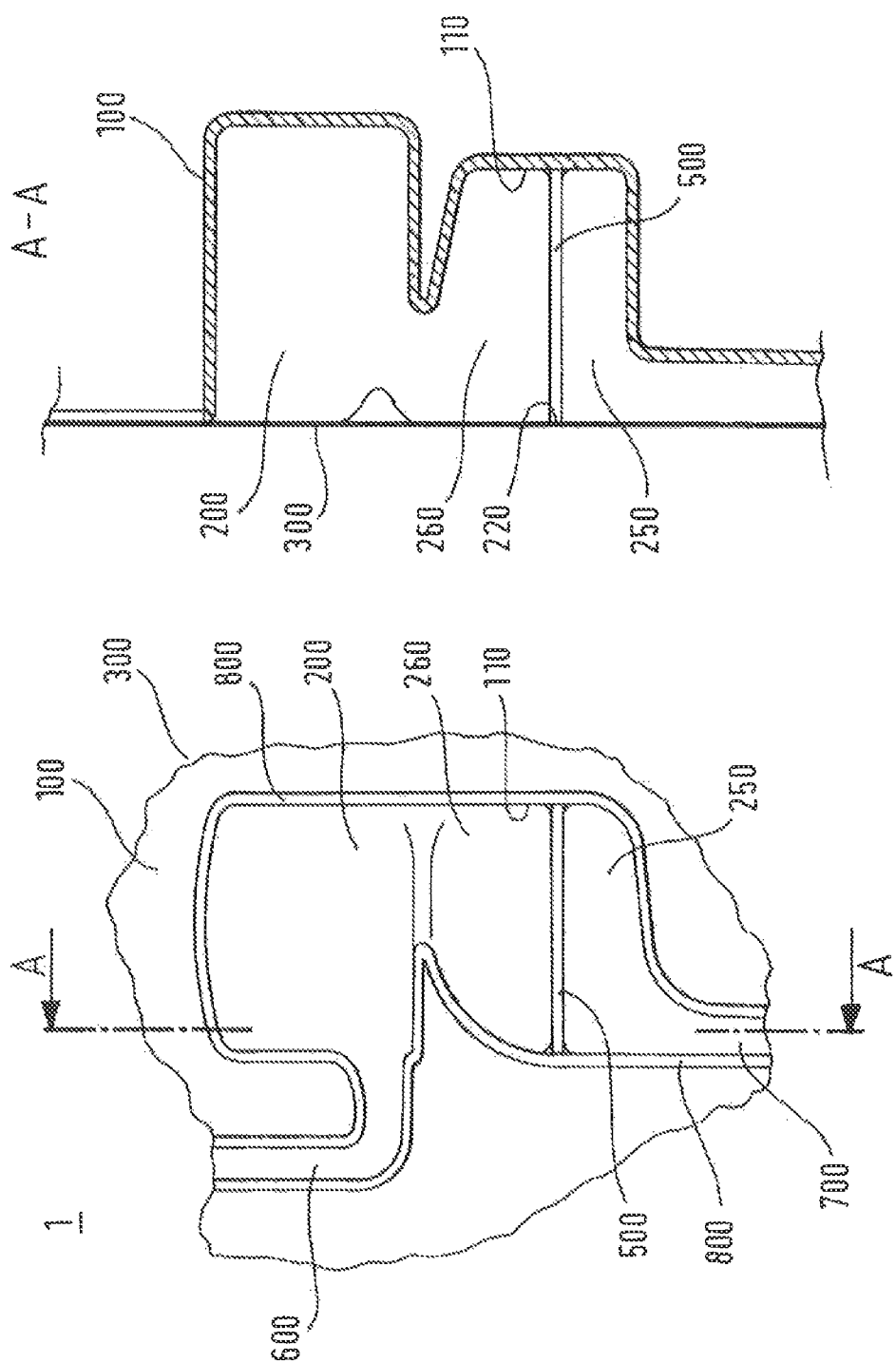
FIG. 1 shows a clear-cut view and a sectional diagram of a detail of a medical fluid cassette according to the invention.
Figure 2:
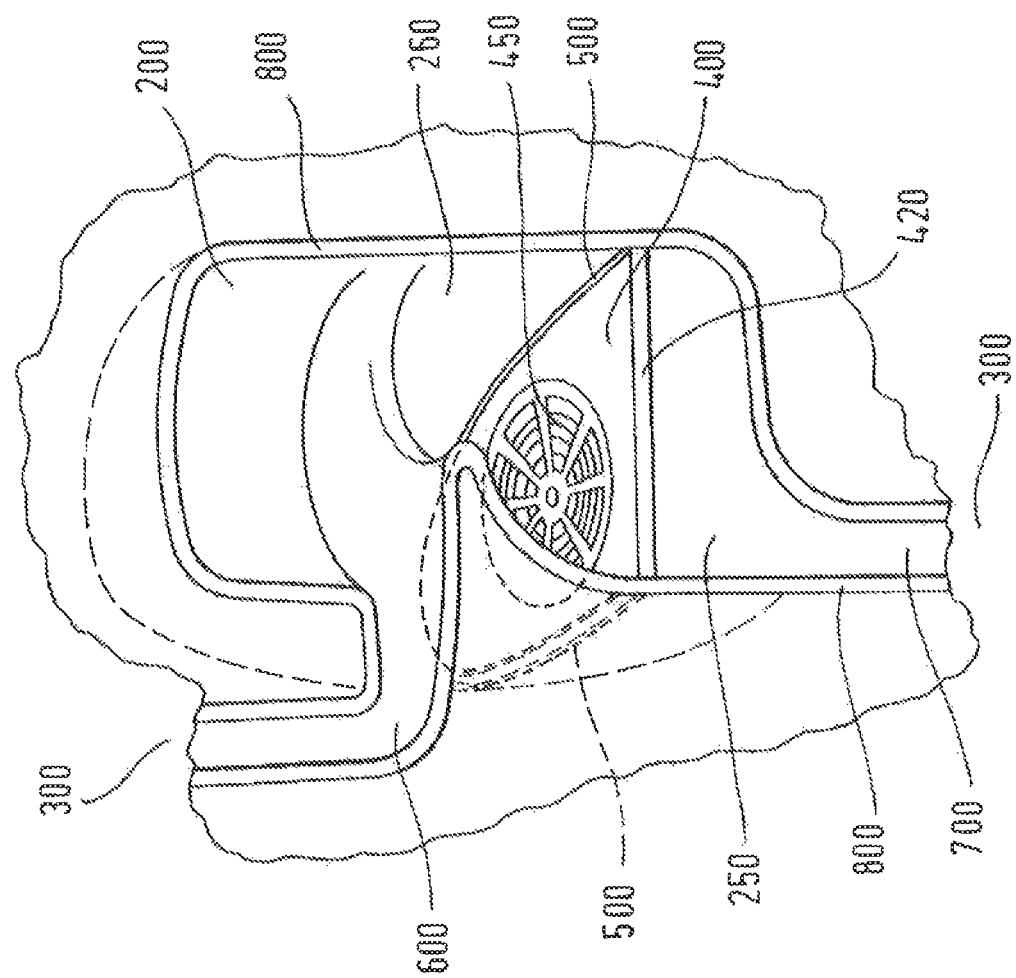
FIG. 2 shows a clear-cut perspective view and a sectional diagram of a detail of a medical fluid cassette according to the invention with the insert according to the invention.
Figure 3:
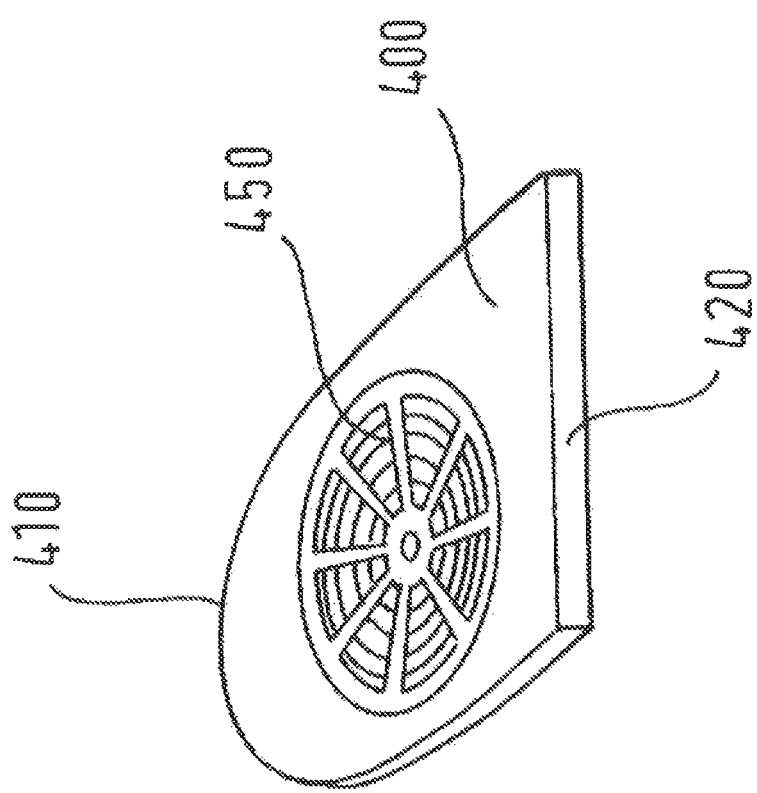
FIG. 3 shows an insert according to the invention with a clot filter for the medical fluid cassette according to FIGS. 1 and 2.

The detail of a medical fluid cassette shown in the present exemplary embodiment in FIGS. 1 and 2 is a schematic drawing. A medical fluid cassette according to the invention may contain additional elements such as valves, measuring sites for pressure and/or temperature, optical measuring sites, inlet lines, outlet lines as well as other chambers and/or channels for receiving and/or carrying medical fluids, for example.

In some embodiments, a medical hose set has a medical fluid cassette according to the present invention.

In special embodiments, a medical hose set with a medical fluid cassette is designed according to the present invention as a blood hose set for the extracorporeal blood treatment.

The medical fluid cassette according to the present invention and/or a medical hose set having a medical fluid cassette according to the present invention is/are suitable and/or provided for use for receiving and/or carrying a medical fluid.

| List of Reference Numerals | |
|---|---|
| Reference Numeral | Name |
| 1 | medical fluid cassette |
| 100 | housing body |
| 110 | first wall section |
| 200 | chamber |
| 220 | second wall section |
| 250 | first chamber section |
| 260 | second chamber section |
| 300 | cover |
| 400 | insert |
| 410 | first peripheral section |
| 420 | second peripheral section |
| 450 | opening structure |
| 500 | receptacle |
| 600 | first fluid channel |
| 700 | second fluid channel |
| 800 | bordering edge |

The invention claimed is:

1. A medical fluid cassette, comprising
   a housing body, which forms a first wall section of a chamber for receiving and/or carrying a medical fluid,
   a cover, which forms a second wall section of the chamber and has a flexible film in at least some sections or is a flexible film in at least some sections,
   a fluid-impermeable insert with a first peripheral section and a second peripheral section, wherein the insert is designed for at least partially filling a cross section of the chamber, wherein the cross section of the chamber is bordered at least by the first wall section and the second wall section, and wherein the insert subdivides the chamber into a first chamber section bordered by the first and second wall sections and a second chamber section bordered by the first and second wall sections, and wherein the fluid-impermeable insert contacts the first and second chamber sections and has at least one opening structure for fluid-permeable connection of the first chamber section to the second chamber section, and
   a receptacle in and/or on the first wall section, wherein the first peripheral section is accommodated in fluid-tight connection with the receptacle.

2. The medical fluid cassette according to claim 1, wherein the second peripheral section is designed for establishing a fluid-tight contact with the flexible film when the flexible film is pressed against the second peripheral section.

3. The medical fluid cassette according to claim 1, wherein the second peripheral section is in permanent fluid-tight connection with the flexible film.

4. The medical fluid cassette according to claim 1, wherein the second peripheral section is designed to be straight and/or wherein the first peripheral section is designed to be curved or angular in at least some sections.

5. The medical fluid cassette according to claim 1, wherein the receptacle has at least one selected from the group consisting of a groove, a web, and a shoulder or is formed therefrom at least in part.

6. The medical fluid cassette according to claim 1, wherein the opening structure has a clot filter.

7. The medical fluid cassette according to claim 1, wherein the first chamber section and/or the second chamber section is designed as an air bubble separator.

8. The medical fluid cassette according to claim 6, wherein the medical fluid cassette is designed for measuring the pressure in the medical fluid upstream from the clot filter and downstream from the clot filter.

9. A medical hose set, having a medical fluid cassette according to claim 1.

10. The medical hose set according to claim 9, wherein the medical hose set is designed as a blood hose set for an extracorporeal blood treatment.

11. Use of a medical hose set according to claim 9 for receiving and/or carrying a medical fluid.

* * * * *